United States Patent [19]

Partos

[11] 4,376,678
[45] Mar. 15, 1983

[54] METHOD OF INHIBITING POLYMERIZATION OF VINYL AROMATIC COMPOUNDS

[75] Inventor: Richard D. Partos, Lunenberg, Mass.

[73] Assignee: American Hoechst Corporation, Somerville, N.J.

[21] Appl. No.: 403,192

[22] Filed: Jul. 29, 1982

[51] Int. Cl.$^3$ .................... B01D 3/32; C07C 7/05; C07C 7/20
[52] U.S. Cl. .................................. 203/9; 203/65; 203/91; 585/4; 585/5; 585/800
[58] Field of Search .................... 203/9, 8, 6, 7, 65, 203/91; 585/1-5, 800, 860; 208/48 AA

[56] References Cited

U.S. PATENT DOCUMENTS

| | | | |
|---|---|---|---|
| 3,476,656 | 11/1969 | Van Tassell et al. | 203/9 |
| 3,520,943 | 7/1970 | Albert | 585/5 |
| 3,526,673 | 9/1970 | Albert | 585/5 |
| 3,527,822 | 9/1970 | Benson, Jr. | 203/9 |
| 3,632,564 | 1/1972 | Albert et al. | 585/5 |
| 3,804,722 | 4/1974 | Oliver | 203/65 |
| 3,816,265 | 6/1974 | Daniels et al. | 203/9 |
| 3,933,599 | 1/1976 | Watson | 203/9 |
| 3,959,395 | 5/1976 | Higgins, Jr. et al. | 585/860 |
| 3,964,978 | 6/1976 | Watson | 203/9 |
| 3,964,979 | 6/1976 | Watson | 203/9 |
| 3,986,937 | 10/1976 | Watson | 203/9 |
| 3,988,212 | 10/1976 | Watson | 203/9 |
| 3,993,547 | 11/1976 | Watson | 203/9 |
| 4,003,800 | 1/1977 | Bacha et al. | 203/9 |
| 4,021,476 | 5/1977 | Harbuck | 203/8 X |
| 4,033,829 | 7/1977 | Higgins, Jr. et al. | 203/9 |
| 4,040,911 | 8/1977 | Bacha et al. | 203/9 |
| 4,040,912 | 8/1982 | Watson | 203/9 |
| 4,050,993 | 9/1982 | Daniels | 203/9 |
| 4,061,545 | 12/1977 | Watson | 203/9 |
| 4,086,147 | 4/1978 | Watson | 203/9 |
| 4,105,506 | 8/1978 | Watson | 203/9 |
| 4,132,601 | 1/1979 | Watson | 203/9 |
| 4,132,602 | 1/1979 | Watson | 203/9 |
| 4,132,603 | 1/1979 | Watson | 203/9 |
| 4,177,110 | 12/1979 | Watson | 203/9 |
| 4,182,658 | 1/1980 | Watson | 203/9 |
| 4,237,326 | 12/1980 | Fuga et al. | 585/4 |
| 4,252,615 | 2/1981 | Watson | 203/9 |

FOREIGN PATENT DOCUMENTS

| | | |
|---|---|---|
| 2148185 | 5/1973 | Fed. Rep. of Germany. |
| 2056481 | 8/1980 | United Kingdom. |
| 237860 | 7/1969 | U.S.S.R.. |
| 679589 | 3/1979 | U.S.S.R.. |

OTHER PUBLICATIONS

V. F. Stroganov et al., "Investigations in the Field of the Synthesis and Reactions of Nitro Derivatives of 2,2-Bis(4-Hydroxyphenyl)Propane", Dnepropetrovsk Chemical & Technological Institute, Translated from Zhurnal Organicheskoi Khimii, vol. 9, No. 8, pp. 1713-1717, Aug. 1973.

*Primary Examiner*—Wilbur L. Bascomb, Jr.
*Attorney, Agent, or Firm*—Tatsuya Ikeda

[57] ABSTRACT

Disclosed is a method of distilling readily polymerizable vinyl aromatic compounds such as styrene, α-methyl styrene, vinyl toluenes and divinylbenzenes wherein 2,2-bis(3,5-dinitro-4-hydroxy-phenyl)propane is used as a polymerization inhibitor. The invention is particularly useful for the distillation of divinylbenzene.

5 Claims, No Drawings

METHOD OF INHIBITING POLYMERIZATION OF VINYL AROMATIC COMPOUNDS

BRIEF SUMMARY OF THE INVENTION

Technical Field

This invention relates to a process for the distillation of readily polymerizable vinyl aromatic compounds. More particularly, this invention relates to a process wherein styrene, substituted styrene, divinyl benzene or polyvinylbenzene is subjected to distillation in the presence of a polymerization inhibitor.

Background Art

Vinyl aromatic compounds such as styrene, α-methyl styrene, vinyl toluene and divinyl benzene tend to polymerize readily, particularly at higher temperatures. In the commercial production of such vinyl aromatic compounds, a purification process is usually required in order to obtain products having an acceptable purity. Since distillation is the usual method employed for such purification, the prevention of the polymerization of such vinyl aromatic compounds during the distillation thereof is a very important subject. Various types of polymerization inhibitors have been employed or suggested in connection with the distillation of vinyl aromatic compounds.

U.S. Pat. No. 3,476,656 describes a method for purifying sulfur-inhibited styrene via a distillation scheme having associated therewith sulfur recovery facilities.

U.S. Pat. No. 3,520,943 describes a method of inhibiting the formation of popcorn polymers during the preparation of synthetic rubbers such as styrene-butadiene copolymer from olefinic monomers which comprises contacting the monomers with an inhibiting amount of a hydroxy benzene tertiary amine oxide compound having the structure

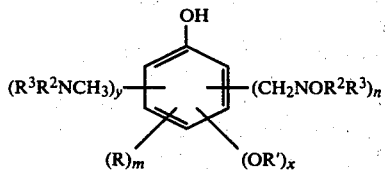

where R is selected from the group consisting of alkyl radicals having from one to eight carbon atoms, chlorine, fluorine, bromine and $NO_2$; m is 0 or 1; R' is selected from the group consisting of hydrogen, alkyl radicals having one to five carbon atoms and a benzyl radical; x is 0 or 1; $R^2$ and $R^3$ are selected from the group consisting of alkyl radicals having one to five carbon atoms, β-hydroxyalkyl radicals having one to five carbon atoms, and oxydiethylene when $R^2$ and $R^3$ together form a single radical; n is 1 or 2; and y is 0 to 1.

U.S. Pat. No. 3,526,673 describes a method of inhibiting the formation of popcorn polymer in processes for the preparation of synthetic rubber from olefinic monomers which comprises contacting the monomers with an inhibiting amount of a tertiary amino dialkyl phenol compound having the structure

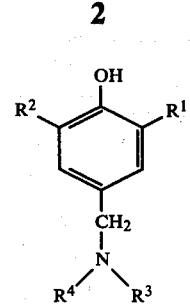

where $R^1$ and $R^2$ are alkyl groups having from one to eight carbon atoms, and $R^3$ and $R^4$ are selected from the group consisting of alkyl radicals having one to five carbon atoms, β-hydroxy-alkyl radicals having one to five carbon atoms, and $R^3$ and $R^4$ combined with the nitrogen atom form a morpholine group.

U.S. Pat. No. 3,527,822 describes a method of inhibiting the polymerization of divinylbenzene which comprises mixing with the divinylbenzene a minor but effective proportion of inhibitor compound selected from the group consisting of 5-methyl-1-nitroso-2-isopropylphenol, 1-nitroso-2-naphthol, 2-nitroso-1-naphthol, and 5-methoxy-2-nitrosophenol.

U.S. Pat. No. 3,632,564 describes a process of retarding the formation of popcorn polymers in monomer recovery systems in the preparation of synthetic rubber from conjugated diolefin-containing monomer systems which comprises contacting said monomer with an inhibiting amount of a compound having the structure,

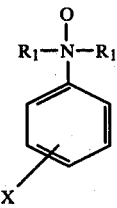

wherein $R_1$ is lower alkyl, hydroxy substituted lower alkyl, or a group of structure

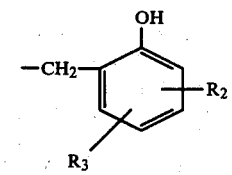

where $R_2$ is hydrogen or lower alkyl, $R_3$ is a tertiary alkyl group, X is hydrogen, halogen, nitro, or lower alkyl, and with the proviso that the total number of carbon atoms in the $R_1$ groups be at least four.

U.S. Pat. No. 3,816,265 describes a process for the distillation of a readily polymerizable aromatic hydrocarbon compound having ethylenically unsaturated substituents, which comprises subjecting such compound to distillation conditions in the presence of N-nitroso diphenyl amine as a polymerization inhibitor and in the absence of oxygen and sulfur.

U.S. Pat. No. 3,933,599 describes a process for the distillation of a readily polymerizable vinyl aromatic compound, which comprises subjecting such compound to distillation conditions in the presence of nitrosyl chloride (NOCl) as a polymerization inhibitor and in the substantial absence of oxygen.

U.S. Pat. No. 3,959,395 describes a process for the recovery and re-use of dinitrophenols employed as inhibitors of polymerization in the distillation and purification of styrene.

U.S. Pat. No. 3,964,978 describes a process for the distillation of readily polymerizable vinyl aromatic compounds in the presence of $NO_2$ used as a polymerization inhibitor.

U.S. Pat. No. 3,964,979 describes a process for the distillation of a readily polymerizable vinyl aromatic compound in the presence of nitric oxide (NO) uses as an inhibitor.

U.S. Pat. No. 3,986,937 describes a process for the distillation of a readily polymerizable vinyl aromatic compound in the presence of $N_2O_3$ used as a polymerization inhibitor.

U.S. Pat. No. 3,988,212 describes a process for the distillation of a readily polymerizable vinyl aromatic compound in the presence of a mixture of N-nitroso diphenyl amine and a dinitro-o-cresol.

U.S. Pat. No. 3,993,547 describes a process for the distillation of a readily polymerizable vinyl aromatic compound in the presence of a polymerization inhibitor comprising an alpha, gamma-bis-diphenylene-beta-phenyl allyl.

U.S. Pat. No. 4,021,476 describes a method of purifying a crude vinyl acetate by distillation wherein a p-alkylphenol having about 4–18 carbon atoms in the alkyl group is used as a polymerization inhibitor.

U.S. Pat. No. 4,003,800 and 4,040,911 describe a method of inhibiting the polymerization of styrene during the vacuum distillation by use of a quinone alkide of the formula

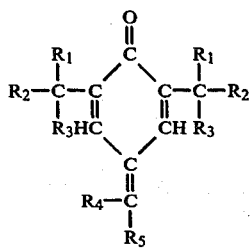

wherein $R_1$, $R_2$ and $R_3$ are either alike or different, members selected from the group consisting of hydrogen, straight or branched chain alkyl moieties having from 1 to 8 carbon atoms, phenyl and alkyl substituted phenyl moieties having up to 9 carbon atoms, cyclic hydrocarbon moieties having from 3 to 5 carbon atoms, and wherein $R_4$ and $R_5$ are either alike or different, members selected from the group consisting of hydrogen, straight or branched chain alkyl moieties having from 1 to 18 carbon atoms, phenyl and alkyl substituted phenyl moieties having up to 9 carbon atoms, and cyclic hydrocarbon moieties having from 3 to 5 carbon atoms.

U.S. Pat. No. 4,033,829 describes a method for inhibiting the polymerization of styrene during distillation wherein dinitrophenol used as an inhibitor is recovered from the styrene still residues and re-used U.S. Pat. No. 4,040,912 describes the distillation of readily polymerizable vinyl compounds in the presence of an adduct of nitric oxide and styrene used as a polymerization inhibitor.

U.S. Pat. No. 4,050,993 describes the distillation of a readily polymerizable aromatic hydrocarbon having ethylenically unsaturated substituents in the presence of N,N-nitroso-methylaniline as a polymerization inhibitor in a system from which oxygen and sulfur have been excluded.

U.S. Pat. No. 4,061,545 describes a process for the distillation of a readily polymerizable vinyl aromatic compound selected from the group consisting of styrene, substituted styrene, divinylbenzene and mixtures thereof, which comprises subjecting said compound to distillation conditions in the presence of an effective amount of a combination of phenothiazine and a phenolic compound as an inhibitor system and also in the presence of oxygen.

U.S. Pat. No. 4,086,147 describes a process for inhibiting the polymerization of a readily polymerizable vinyl aromatic compound during the distillation thereof, wherein m-nitro-p-cresol is used as an inhibitor.

U.S. Pat. No. 4,132,601 describes the distillation of a readily polymerizable vinyl aromatic compound in the presence of an effective amount of polymerization inhibitor selected from the group consisting of 3-nitro-2,5-cresotic acid or 3-nitro-2,5-cresotaldehyde.

U.S. Pat. No. 4,105,506 describes the distillation of readily polymerizable vinyl aromatic compound in the presence of a polymerization inhibitor comprising 2,6-dinitro-p-cresol.

U.S. Pat. No. 4,132,602 describes the distillation of readily polymerizable vinyl aromatic compounds in the presence of 2-halo-6-nitro-p-cresol.

U.S. Pat. No. 4,132,603 describes the distillation of readily polymerizable vinyl aromatic compounds in the presence of 4-halo-3,5-dinitrotoluene used as a polymerization inhibitor.

U.S. Pat. No. 4,177,110 describes the use of a combination of phenothiazine and tertiarybutylcatechol for the distillation of readily polymerizable vinyl aromatic compounds.

U.S. Pat. No. 4,182,658 describes the use of 2,6-dinitro-p-cresol or m-nitro-p-cresol for inhibiting the polymerization of a readily polymerizable vinyl aromatic compound under an emergency condition during the distillation thereof.

U.S. Pat. No. 4,237,326 describes a method of inhibiting the polymerization of styrene with an inhibitor selected from 2-methylbenzoquinone-4-oxime, 2,3,5-trimethylbenzoquinone-4-oxime or a mixture thereof.

U.S. Pat. No. 4,252,615 describes a method for the distillation of a readily polymerizable vinyl aromatic compound employing 2,6-dinitro-p-cresol.

German Offenlegungsschrift No. 2,148,185 describes a polymerization inhibitor for polymerizable vinyl group containing aliphatic, aromatic and heterocyclic compounds which is a mixture of (A) a thiobisphenol of the general formula

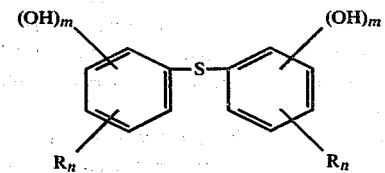

where R is an alkyl of 1–4 carbons, n is 1, 2 or 3 and m is 1 or 2; and (B) a p-alkoxyphenol of the general formula

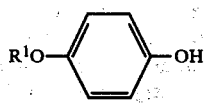

where $R^1$ is an alkyl of 1–4 carbons.

United Kingdom Patent Application GB 2,056,481A describes a distillation process of styrene wherein a nitrosophenol is fed as a polymerization inhibitor in the form of a solution thereof in a solvent (A) which is at least one solvent selected from alcohols, ketones, and aldehydes each being in liquid state and having a boiling point lower than 100° C., or in a solvent (B) comprising a mixture of a solvent (A) and an aromatic compound.

USSR Pat. No. 679,589 describes a method of inhibiting thermal polymerization of styrene wherein 0.05–1% by weight of 2,4-dinitro-1-naphthol is added to styrene.

It is important that polymerization inhibitor possess not only a strong inhibiting property but also other practical advantages. For example, it is very desirable that the inhibitor does not cause ecological problems in the disposal of the distillation still residues and that it does not contaminate the purified product. Where the inhibitor is toxic, or has an undesirable effect on the end applications of the vinyl aromatic compound, the amount of carried-over inhibitor in the purified product should be very low. This means that a polymerization inhibitor should possess a suitable vapor pressure and thermal stability at distillation temperatures.

Thus, it is an object of the present invention to provide a new polymerization inhibitor which is effective for preventing the polymerization of readily polymerizable vinyl aromatic monomers under distillation conditions, particularly vacuum distillation conditions and which also possesses a high thermal stability and a low tendency to be carried over to the distilled product. It is another object of the invention to provide a new polymerization inhibitor for vinyl aromatic monomers which does not cause ecological problems in the disposal of the distillation still residues.

Other objects, features and advantages of the invention will become apparent from the following description of the invention.

DISCLOSURE OF THE INVENTION

Purification of readily polymerizable vinyl aromatic compounds such as styrene, α-methyl styrene, vinyl toluenes and divinylbenzenes is conducted by subjecting the compounds to a vacuum distillation condition in the presence of 2,2-bis(3,5-dinitro-4-hydroxy-phenyl)-propane which is used as a polymerization inhibitor. This invention is particularly useful for the distillation of divinylbenzene.

DETAILS OF THE INVENTION

This invention provides a process for the vacuum distillation of readily polymerizable vinyl aromatic monomers.

The term "readily polymerizable" as used in the specification and the appended claims shall mean that the rate of thermal polymerization of the compound at its reflux temperature under atmospheric pressure is such that at least 1 gram of polymer is formed from 100 grams of pure monomer after 6 hours of reflux.

The term "vinyl aromatic monomer" as used herein shall mean an aromatic monomer having at least one vinyl group. Examples of "readily polymerizable vinyl aromatic monomers" include styrene, α-methyl styrene, vinyl toluenes and divinylbenzenes.

This invention uses 2,2-bis(3,5-dinitro-4-hydroxyphenyl) propane as a polymerization inhibitor. For the sake of convenience, this compound will also be called tetranitrobisphenol A. A method of synthesizing said compound is described in Stroganov et al, Zh. Org. Khim 1973, 9(8), 1713–17, and Smirnov and Stroganov USSR Pat. No. 237,860 (1969). Thus, 2,2-bis(4-hydroxyphenyl)propane is nitrated with a concentrated nitric acid (for instance 70% $HNO_3$) in a suitable solvent such as dichloroethane to afford primarily 2,2-bis(4-hydroxy-3-nitro-phenyl)propane. A typical reaction condition for this step is 20°–30° C. for 2 hours. Without isolating the product, a mixture of sulfuric acid and nitric acid (for instance, 42% $H_2SO_4$, 50% $HNO_3$, and 8% $H_2O$) is added to the reaction mixture and nitration continued to afford tetranitrobisphenol A. A typical reaction condition for the second step is 40° C. for 2 hours. The desired product is isolated by a routine procedure.

The tetranitrobisphenol A inhibitor may be introduced into the distillation system in any convenient manner which permits an efficient distribution of the inhibitor throughout the distillation system. A preferred mode of introduction is simply to add the inhibitor to the crude feed stream. The polymerization inhibitor may be added to the system either continuously or intermittently. For the sake of better control of the inhibitor concentration, however, it is generally preferable to add the inhibitor continuously.

The amount of the polymerization inhibitor used in the present invention to inhibit the polymerization of vinyl aromatic compounds may vary over a broad range depending upon many factors including the identity of the compound to be distilled, the feed stream composition, the degree of inhibition desired, the distillation conditions such as the temperature, pressure, reflux ratio, residence time, design of the distillation apparatus etc. Needless to say, different vinyl aromatic compounds have different tendencies for thermal polymerization, and generally speaking the larger the amount of inhibitor used the larger is the effect of inhibition of polymerization. Excessive amounts of inhibitor should be avoided, however, for various reasons such as increased cost of the inhibitor and increased risk of contamination of the distilled product. In the case of styrene vacuum distillation, a preferred concentration range of the inhibitor is typically 30–3,000 ppm by weight with respect to the amount of the crude feed stream, a more preferred range being 100–2,000 ppm. In the case of divinylbenzene vacuum distillation, a preferred concentration range is typically 100–10,000 ppm, a more preferred range being 500–5,000 ppm.

Although this invention is generally useful for the vacuum distillation of various readily polymerizable vinyl aromatic compounds such as styrene, α-methyl styrene, vinyl toluene, and divinylbenzene, it is particularly useful for the vacuum distillation of divinylbenzene.

Divinylbenzene is generally produced commercially by a catalytic dehydrogenation of a mixture of the isomers of diethylbenzene. Such mixtures of diethylbenzene isomers are usually produced as a by-product of a process for making ethylbenzene by the Friedel-Crafts ethylation of benzene. Products obtained from dehydrogenation of diethylbenzenes generally contain a mixture of divinylbenzenes, ethylvinylbenzenes, unreacted diethylbenzenes, a small quantity of naphthalene, and some impurities. Thus, a typical feed stream for the divinylbenzene distillation system comprises low boiling materials (such as styrene and ethylbenzene), diethylbenzene, ethylvinylbenzene and divinylbenzene.

The boiling points of the 1,3-isomers of diethylbenzene, ethylvinylbenzene and divinylbenzene, which are usually the predominant isomers in the distillation feed stream, are 181° C., 191.5° C., and 199.5° C., respectively. The other isomers have similar boiling points. In order to purify divinylbenzene from such crude feed stream a series of distillation columns typically consisting of four columns is used. The first column removes low boiling materials from its overhead, the second column removes diethylbenzene and a part of ethylvinylbenzene from its overhead, the third column removes ethylvinylbenzene from its overhead and the fourth column removes divinylbenzene from its overhead as a desired product. Since pure divinylbenzene has a high tendency to polymerize, commercial products of divinylbenzene are usually produced as a mixture of divinylbenzene and ethylvinylbenzene, a typical concentration of divinylbenzene in such commercial products being about 55%.

During vacuum distillation of divinylbenzene, the temperature of the reboiler is preferably maintained at from 150° F. to about 260° F. by controlling reboiler pressure at from about 30 mm Hg to about 400 mm Hg.

The polymerization inhibitor exits from the distillation system as a constituent of the high boiling residue. Disposal of such residue can be accomplished simply by burning. Such disposal of the residue by burning does not cause any significant ecological problems. This is a distinct advantage over a method employing sulfur or sulfur in combination with other compounds as a polymerization inhibitor where a heavy bottom material is formed which is valueless for further use and constitutes a polluting material which must be disposed of.

Tetranitrobisphenol A used in this invention has a lower boiling point than most of the conventional polymerization inhibitors used for the vacuum distillation of vinyl aromatic compounds such as those inhibitors mentioned earlier in the section describing the background art. Tetranitrobisphenol A at the same time is an effective polymerization inhibitor for readily polymerizable vinyl aromatic compounds at concentration levels commonly used for the conventional polymerization inhibitors. Thus, the present invention reduces the risk of carry-over of the inhibitor into the distilled product while at the same time accomplishing a desired degree of inhibition of thermal polymerization of the material. Commercially, this is a very significant advantage, particularly in light of the current trend for more stringent government regulations regarding safety and health hazzards of chemical products.

The following examples are presented merely for the purpose of illustrating this invention.

EXAMPLE 1

Tetranitrobisphenol A, dinitrobisphenol A and dinitrosecondarybutylphenol were tested for their effect of inhibiting the thermal polymerization of styrene. In each experiment 350 ml of purified styrene monomer was placed in a flask and an inhibitor in the amount of 275 ppm by weight with respect to styrene was added. The content of the flask was heated to 100° C. and maintained at that temperature. Fifty milli-liter samples were taken from the flask at the end of 2, 4, and 6 hours of heating at 100° C. in order to determine the amounts of polymers formed. Polymer contents of the liquid samples were determined by pouring each liquid sample into 500 ml of methanol, collecting precipitated material and weighing it after drying. From this, percentage of polymer formation after each heating period was calculated. The results of polymer formation for the three materials were as follows:

| Inhibitor | 2 Hours | 4 Hours | 6 Hours |
|---|---|---|---|
| Tetranitrobisphenol A | 0.01% | 0.04% | 0.07% |
| Dinitrosecondarybutylphenol | 0.04% | 0.08% | 0.10% |
| Dinitrobisphenol A (Source 1) | 0.06% | 0.21% | 0.45% |
| Dinitrobisphenol A (Source 2) | 0.08% | 0.34% | |

EXAMPLE 2

Divinylbenzene distillation runs were conducted using tetranitrobisphenol A, dinitrosecondarybutylphenol and dinitrobisphenol A polymerization inhibitors and the carry-over tendencies of these compounds were evaluated. A divinylbenzene composition comprising about 75% divinylbenzenes (the remainder being primarily ethylbenzenes) which was obtained from a commercial scale distillation of a crude divinylbenzene feed stream was used for the experiment. In this experiment, a pilot plant scale distillation apparatus having in the column an adjustable number of distillation trays made of perforated stainless steel was used. For each inhibitor, a series of runs was conducted by changing the number of trays placed in the distillation column. The inhibitor compositions in the feed liquid were 3000 ppm, 4000 ppm, and 5000 ppm by weight for runs using tetranitrobisphenol A, dinitrosecondarybutylphenol, and dinitrobisphenol A, respectively. These concentrations were chosen in order to maintain a comparable inhibitory effect among the three series of runs. The vapor pressure at the distillation head was maintained at about 10 mm Hg. Distillate samples were removed from the head after a steady distillation condition had been reached. The amounts of inhibitors carried-over to the distillates were determined by use of a polarographic method. The concentrations of the inhibitors in the distillate samples were as follows:

| Number of trays used | Concentration of the Inhibitor carried over |
|---|---|
| (a) Runs using tetranitrobisphenol A | |
| 3 | less than 0.005 ppm |
| 5 | " |
| 8 | " |
| 10 | " |
| 15 | " |
| (b) Runs using dinitrosecondarybutylphenol | |
| 3 | 0.09 ppm |
| 5 | 0.03 ppm |
| 10 | 0.04 ppm |
| 15 | 0.02 ppm |
| (c) Runs using dinitrobisphenol A (Source 2) | |
| 3 | less than 0.005 ppm |
| 5 | " |
| 8 | " |

I claim:

1. A method of distilling a readily polymerizable vinyl aromatic compound, which comprises subjecting said compound to a vacuum distillation condition in a distillation system in the presence of 2,2-bis(3,5-dinitro-4-hydroxy-phenyl) propane.

2. A method according to claim 1, wherein said vinyl aromatic compound comprises divinylbenzene.

3. A method according to claim 1, wherein said vinyl aromatic compound comprises styrene.

4. A method according to claim 1, wherein said vinyl aromatic compound comprises α-methyl styrene.

5. A method according to claim 1, wherein said vinyl aromatic compound comprises vinyl toluene.

* * * * *